(12) United States Patent
Oshio et al.

(10) Patent No.: US 7,020,318 B2
(45) Date of Patent: Mar. 28, 2006

(54) TRANSLUCENT INTENSITY PROJECTION IMAGING

(75) Inventors: Koichi Oshio, Santa Rosa, CA (US); David A. Feinberg, Bodega Bay, CA (US); Matthias Guenther, Sebastopol, CA (US)

(73) Assignee: Advanced MRI Technologies, LLC, Sebastopol, CA (US)

( * ) Notice: Subject to any disclaimer, the term of this patent is extended or adjusted under 35 U.S.C. 154(b) by 677 days.

(21) Appl. No.: 10/153,993

(22) Filed: May 22, 2002

(65) Prior Publication Data

US 2003/0097057 A1    May 22, 2003

Related U.S. Application Data

(60) Provisional application No. 60/292,785, filed on May 22, 2001.

(51) Int. Cl.
*G06K 9/00*    (2006.01)

(52) U.S. Cl. .................... 382/131; 382/130; 382/132; 600/410; 128/922

(58) Field of Classification Search ................ 382/128, 382/129, 130, 131, 132, 133, 134; 604/410, 604/407; 324/307; 436/173; 250/455; 128/922
See application file for complete search history.

(56) References Cited

U.S. PATENT DOCUMENTS

| | | | |
|---|---|---|---|
| 5,150,421 A  * | 9/1992 | Morishita et al. ........... 382/169 |
| 5,368,033 A  * | 11/1994 | Moshfeghi .................. 600/419 |
| 6,519,354 B1 * | 2/2003 | Oshio .......................... 382/130 |
| 2002/0168321 A1 * | 11/2002 | Tournier et al. ........... 424/9.32 |

* cited by examiner

*Primary Examiner*—Kanjibhai Patel
*Assistant Examiner*—Ali Bayat
(74) *Attorney, Agent, or Firm*—Cooper & Dunham LLP

(57) ABSTRACT

MR imaging produces a projection image showing better image contrast between small blood vessels and background than traditional net intensity projection (NIP) images but more visual clues to vessel depth than traditional maximum intensity projection (MIP) images.

6 Claims, 5 Drawing Sheets

TRANSLUCENT INTENSITY PROJECTION IMAGING

REFERENCE TO RELATED APPLICATION

This present application claims the benefit of provisional Application Ser. No. 60/292,785, filed on May 22, 2001, which is hereby incorporated herein by reference.

FIELD

This patent specification is in the fields of magnetic resonance imaging (MRI), magnetic resonance angiography (MRA), computerized tomography (CT) and similar imaging and more particularly relates to deriving a selected two-dimensional (2D) projection of information of interest contained in a three-dimensional (3D) image.

BACKGROUND AND SUMMARY

A number of imaging methods and techniques have been used to visualize blood vessels in vivo but have demonstrated limitations pointing to a need for a new way to produce better results.

For example, a state-of-the-art MRA method, the maximum intensity projection (MIP), may not accurately show areas where blood vessels overlap in the 2D projection. On the other hand, volume rendering method of MRA data might depict such overlap more accurately but at the expense of overall reduced contrast-to-noise ratio (CNR) that can obscure small vessels and the expense of the need to adjust two independent variable parameters and thus make routine clinical usage difficult.

A much earlier method of imaging blood vessels in vivo is conventional x-ray angiography, in which a contrast agent is injected into the patient's arterial system and x-ray images are acquired that show blood vessels as translucent high-intensity areas. Where two vessels overlap, the image is brighter than for the individual vessels. Seeing through vessels and being able to identify overlapping vessels permits an analysis to determine relationships and origins of branching vessels and depth of vessels in the body and thus enable effective spatial interpretation of the x-ray arteriogram.

Angiographic images created by MRI techniques can show vessels in a patient's body but may not compare favorably with conventional x-ray angiograms in terms of contrast relative to the surrounding tissue and contrast-to-noise ratio (CNR), thus making it difficult in some cases to distinguish blood vessels from the surrounding tissue. MRA is a 3D technique, as opposed to 2D x-ray angiography, but the 3D information is not visualized directly so a projection method is used to produce 2D MRA information. First, the 3D information is assembled from many MRI slices, which are essentially 2D images, by piecing them together with known software to form a 3D set of data representing the volume of interest in the patient. Typically, the blood vessels in this volume are represented by the more intense pixels (or voxels). However, their intensity is not much greater than that of the surrounding tissue.

One way to better separate data representing blood vessels from data representing surrounding tissue is to use the maximum intensity projection (MIP) method, which has a particularly high CNR. (See Ref. 1 cited in the endnotes and note that the contents of each reference cited in the endnotes are hereby incorporated by reference in this patent specification.) This method creates a projective 2D image of the vessels contained in the volume represented by the 3D data. To construct the 2D image, the MIP method forms a set of notional (imaginary) rays extending through the 3D data, with a respective ray for every pixel in the 2D image and with each data point (for pixel or voxel) in the 3D image being intersected by only a single ray. For a given ray, the MIP method selects the single most intense data point that the ray intersects and uses that data point to control the brightness (value) of the pixel in the 2D image associated with that ray. This process continues to create a 2D image composed of the pixels associated with all the rays. Methods to further improve CNR and the signal-to-noise ration (SNR), and thus improve the visualization of blood vessels, have been proposed. See Refs. 2, 3.

For example, the 3D MRA information may comprise 256×256×256 data points that represent a corresponding 3D array of pixels or voxels in the patient's body. Of course, the data point array need not be stored as a 3D array so long as the relationship between a data point and its 3D position can be ascertained when needed. The projective 2D image representing the 3D array may contain 256×256 pixels. To construct the 2D image, 256×256 notional rays, one for each pixel in the 2D image, are extended through the 3D array, with each ray notionally intersecting 256 data points in the 3D array for the example of non-rotated projections. For each ray, the single most intense data point of the 256 points the ray intersects is selected, and the value of this single data point from the 3D array is used to control the display of the associated pixel in the 2D image. Proposals have been made to refine this general approach to MIP but are not believed to have found widespread clinical applications, probably due to CNR limitations. See Refs. 4–6.

The MIP method has a number or limitations. One is that only one of the (256) data points of the 3D array that a ray intersects is used in constructing the 2D image. In this example 255 out of 256 data points are not used in the construction of the 2D image except to the extent of identifying the one point to be used. Important details and valuable information can be lost by not making more use of the vast majority of the information in the 3D array. For example, if two vessels overlap each other in the 2D projection, the MIP method will use information from only one of the vessels, not from both, to show the overlap area in the 2D image, because only one data point from the 3D array can be selected for any one ray. Only the vessel in the foreground or the vessel in the background will be shown but not both. This can lead to misrepresentation of relative positions of vessels in the 2D image. It also causes a generally flat appearance of vessels in the MRA image produced by the MIP method as many of the depth perception visual clues are missing from the image.

One improvement on the MIP method is referred to as net intensity projection (NIP) and is discussed in a provisional application filed September 1998 by Koichi Oshio, entitled "Method and Apparatus for Projecting MR Angiographic Data". Instead of selecting only the single most intense data point in the 3D array that an imaginary ray intersects, the NIP method selects all of the more intense points, i.e., all the data points above a selected intensity threshold. The pixel value in the 2D image that corresponds to this ray is calculated by adding up the values of the selected points from the 3D set, with appropriate normalizing if desired. Because typically several data points from the 3D set are used to represent a vessel pixel in the 2D image, instead of the single point for a MIP image, the NIP method produces a 2D image that can give visual clues about the 3D structure of the vessels. Overall appearance of the projection image can be more akin to conventional angiograms. Larger blood vessels can look more intense than smaller vessels, and overlapping portions of blood vessels running toward the observer can have higher intensity. Since background data points in the 3D image typically have lower intensity, most data points from the 3D image that correspond to non-vessel tissue are not added in when calculating the pixel values for the 2D image. Therefore, it is possible to maintain good contrast between vessels and background tissue. However, compared to the MIP method, the 2D images from the NIP method can make it more difficult to visualize small vessels.

Another known method of inspecting the 3D data set is to use 3D rendering techniques. They are generally divided into two classes, surface rendering (SR) and volume rendering (VR). SR involves a geometric reconstruction of the scalar valued 3D MRA data set using triangular meshes for example. The geometric representation can be visualized by known 3D graphic algorithms including color, shading and additional surface properties. Since for this purpose the surface properties of the blood vessels have to be detected first, this method tends to be time consuming and also error-prone for noisy data. Methods have been proposed to post-process MRA data but are not believed to have achieved much success. See Refs. 7–9. Volume rendering (VR) creates 2D images from the 3D data set by taking into account all or most of the 3D data points, unlike MIP. However, the vast majority of the data points in the 3D set represents tissue other than the blood vessels of interest. When the many data points representing other tissues are combined with the relatively few points representing vessels, they can overwhelm the information of interest. The resulting image may contain details showing how blood vessels overlap at different depths but other details can be washed out due to the inclusion of surrounding tissue. For example, in displaying small blood vessels the CNR can be greatly reduced in the VR method as compared with the MIP method. Parameters such as the values of data points in the 3D array can be attenuated if they are likely to represent tissue other than blood vessels. In addition, VR suffers from the difficulty that the parameters of shading and intensity must be selected and adjusted by the operator. These two parameters are not directly related to the familiar "window" and "level" with which MRI technologists are experienced. For these and other reasons, the robustness and consistency of creating and displaying VR images compared with the MIP method is a problem that has limited the acceptance and utilization of VR for this application. The longer operator time required to obtain a satisfactory result with VR compared with MIP can be a significant economic issue given the expense of additional scanner time and operator time.

To overcome these and other limitations, a new approach has been developed, called "translucent intensity projection" (TIP) in this patent specification. TIP makes a particularly efficient use of relevant information from the 3D data set but removes undesired effects of unneeded or deleterious information. The TIP approach can allow the operator to dial in as much 3D information as desired, in a way that can be conceptualized as a synergistic combination of MIP and NIP features. TIP can produce significantly superior results while avoiding issues presented by the SR and VR methods.

The TIP method both achieves high sensitivity (CNR and SNR), a characteristic present in MIP but absent from NIP images, and provides 3D visual clues in the 2D image, a characteristic present in NIP but absent from MIP images. This gives TIP images high image contrast between small vessels and the background but also 3D visual clues.

Whereas MIP applies 100% weight to the most intense data point in the 3D image that a ray intersects and 0% weight to all other points this ray intersects, and NIP applies the same weight to the set of N more intense points that the ray intersects, TIP applies a high weight to the point that MIP would pick and lower but still significant weights to adjacent or nearby points along the ray path. Some or all of these points may also have been picked in NIP, but NIP applies the same weight to all picked points, including the point that MIP would have picked.

An additional improvement disclosed in this patent specification is called "local net intensity projection" (LNIP) and involves using for the 2D projection more of the 3D points that MIP but less than NIP, and selects the points to be used in a way designed to show small vessels and also retain visual clues on vessel depth in the body.

DETAILED DESCRIPTION OF PREFERRED EMBODIMENTS

Features of different vessel visualization techniques can be assessed by processing an identical set of MRI data. In a specific and non-limiting example used here, a cardiovascular MR scanner, a Siemens Sonata 1.5T scanner, was used to obtain the data. A set of non-contrast data was obtained followed by a corresponding set after a bolus injection of 10–20 cc gadolinium contrast agent, using a conventional 3D contrast-MRA protocol. The scanner's gradient performance was considered sufficient (40 mT/m with 200 slew rate) to obtain breath-hold 3D contrast-MRA data in 18–25 seconds. The non-contrast MRA data set was used to mask the background signal from fat and other short-T1 structures, as is conventional, resulting in a corrected 3D data point set. An off-line computer was then used to calculate MIP and VR images using conventional software, and to calculate NIP and TIP images using methods described here. The calculated MIP, VR, NIP, and TIP images were transferred back to the MR scanner for use of the scanner display software and filming capability via a Kodak dry view printer.

Conceptually, the process of deriving a 2D image from a 3D set of MRI data points starts with the corrected 3D data point set, where each data point has a value related to a voxel in the imaged patient value. As earlier noted, the data point values may be stored in any suitable memory so long as the system keeps track of their relationship to voxel positions in the body. In principle, the process involves casting imaginary rays through the 3D volume of voxels and using values of data points for relevant voxels intersected by the rays in a different way to calculate pixel values for the 2D image at locations positionally related to the rays.

Figure 1:
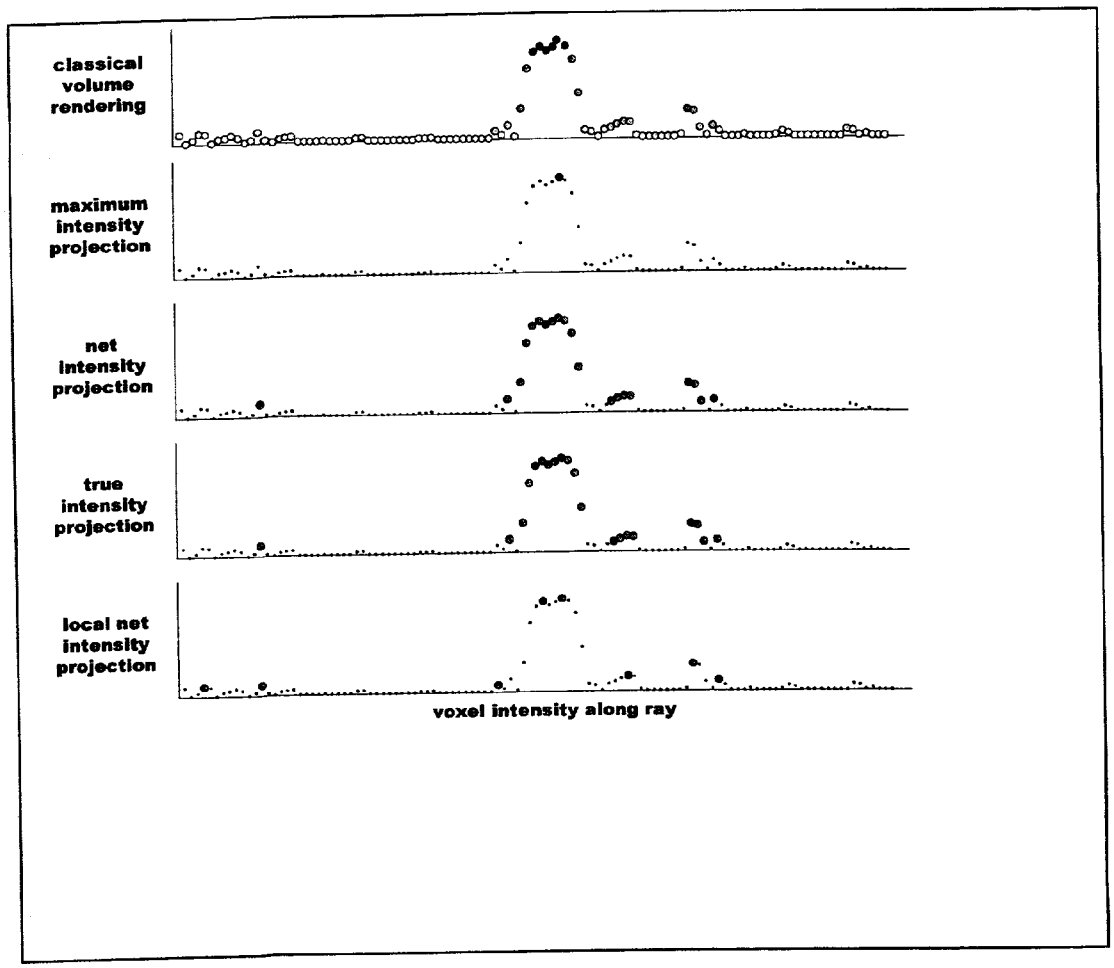
FIG. 1 illustrates ways to select data points (voxels) of a 3D image for use in calculating a pixel value in a 2D projective image for a given imaginary ray intersecting these data points. Used data points are represented by bigger circles, unused ones by smaller circles, and the shade of gray represents a weighting factor (darker means more weight).

Referring to FIG. 1, the top graph labeled "classical volume rendering" illustrates the values of data points for voxels intersected by one of the imaginary rays. Each circle represents a data point, the vertical position of the circle represents the value of the data point, large circles (as in this case) mean that the data points are used to calculate the value of a pixel in the 2D image, and the gray value of a circle represents the weighting of the data point value in the calculation of the pixel value. In the case of VR, all data points are used but those of highest intensity are given more weight. The data points along a ray are used to calculate the value of a pixel in a 2D image projected on a plane normal to the ray and notionally positioned relative to the 3D volume such that the ray would intersect the pixel.

The second graph in FIG. 1 is labeled "maximum intensity projection." Here, only a single data point contributed to the relevant pixel in the MIP 2D image—the highest-intensity data point; all others are disregarded.

The third graph is labeled "net intensity projection." Here, all data points that have intensities above a selected, relatively low threshold contribute to the relevant pixel, but are assigned the same weights, that is, each makes the same type of contribution to the pixel value. To calculate an entire 2D image, first the user decides from what perspective to view the 3D data. The process that follows can be conceptualized as extending, from each pixel in the 2D image plane, a ray normal to the plane and passing through the imaged 3D volume. For each ray, the values of intersected voxels in the 3D volume that exceed a low threshold are summed and the pixel value is calculated based on that sum.

The fourth graph is labeled "true intensity projection" and relates to the translucent intensity projection or TIP method that is the subject of this patent specification. Here, all data points above a selected, low threshold are used to calculate the value of the relevant pixel, but in different weights, i.e., different proportions of the data points are used depending on the values on the data points. The highest intensity data point is given a greater weight than the other points that are used, i.e., the highest intensity data point from the corrected 3D data set that corresponds to the relevant imaginary ray contributes more to the value of the relevant pixel in the 2D image than the other data points that also contribute to the pixel value.

As a simplified alternative, a type of a TIP image can be obtained by adding a MIP and NIP images for the same projection. The MIP image contributes high image contrast between small vessels and the background while the NIP image contributes an intensity variation in vessels. The intensity variation dependence on the vessel diameter can be somewhat less as compared with a TIP image in which more than two different weights are applied to the relevant 3D data points but some visual clues to vessel depth are still present.

Through reasonable experimentation, a weight distribution for the TIP image can be derived that gives a desired balance between visualization of small vessels and depth information clues for all cases or for respective classes of cases. For example, adding the MIP and NIP images can be characterized as assigning a high weight to the most intense data point along a ray and identical lower weights to all other points for the same ray that contribute to the relevant pixel value in the 2D image. A more sophisticated method is to assign linearly higher weights to higher-intensity data points that contribute to a pixel. If the slope of the weighting function is steeper, smaller vessels and edges of larger vessels become more prominent in the 2D image. The weighting function need not be linear with data point intensity. It can have an initial steep slope to emphasize edges of vessels but then flatten, or it can have other shapes that reasonable experimentation shows give desirable results. It is believed to be preferable to have the weighting function increase monotonically with data point intensity.

Another method that is the subject of this patent specification is illustrated conceptually in FIG. 1 at the graph labeled "local net intensity projection." In TIP, blood vessels overlapping with very large vessels might not be visualized well when most of the higher intensity data points that contribute to the pixels in the relevant part of the 2D image come from the larger vessel. As illustrated in the bottom graph in FIG. 1, if the larger vessel contains many more voxels intersected by the relevant imaginary ray that a small vessel intersected by the same ray, the data points for the larger vessel could overwhelm those for the smaller vessel. A solution to this in accordance with the patent specification is illustrated in the bottom graph of FIG. 1 and involves making sure that smaller vessels also make a significant contribution to the 2D image. In this example of LNIP, this is accomplished by using only non-adjacent maximum intensity data points in the calculation for the relevant pixel. Stated differently, each local peak in the values of the 3D data points related to a ray, where the local peak is above a threshold, contributes a single data point, suitably weighted, to the calculation of the relevant pixel in the 2D image. This example is not limiting, and other ways can be devised through reasonable implementation to account for local peaks that are likely to represent smaller blood vessels. For example, instead of using only one point from a local peak, more points can be used from a wider peak, or from a steeper peak, and different weights can be assigned to higher peaks, based on the results of reasonable experimentation to identify weighting schemes that reflect this principle and give desired 2D image characteristics such as visualizing small vessels well while also showing well visual clues of depth information.

Figure 2:
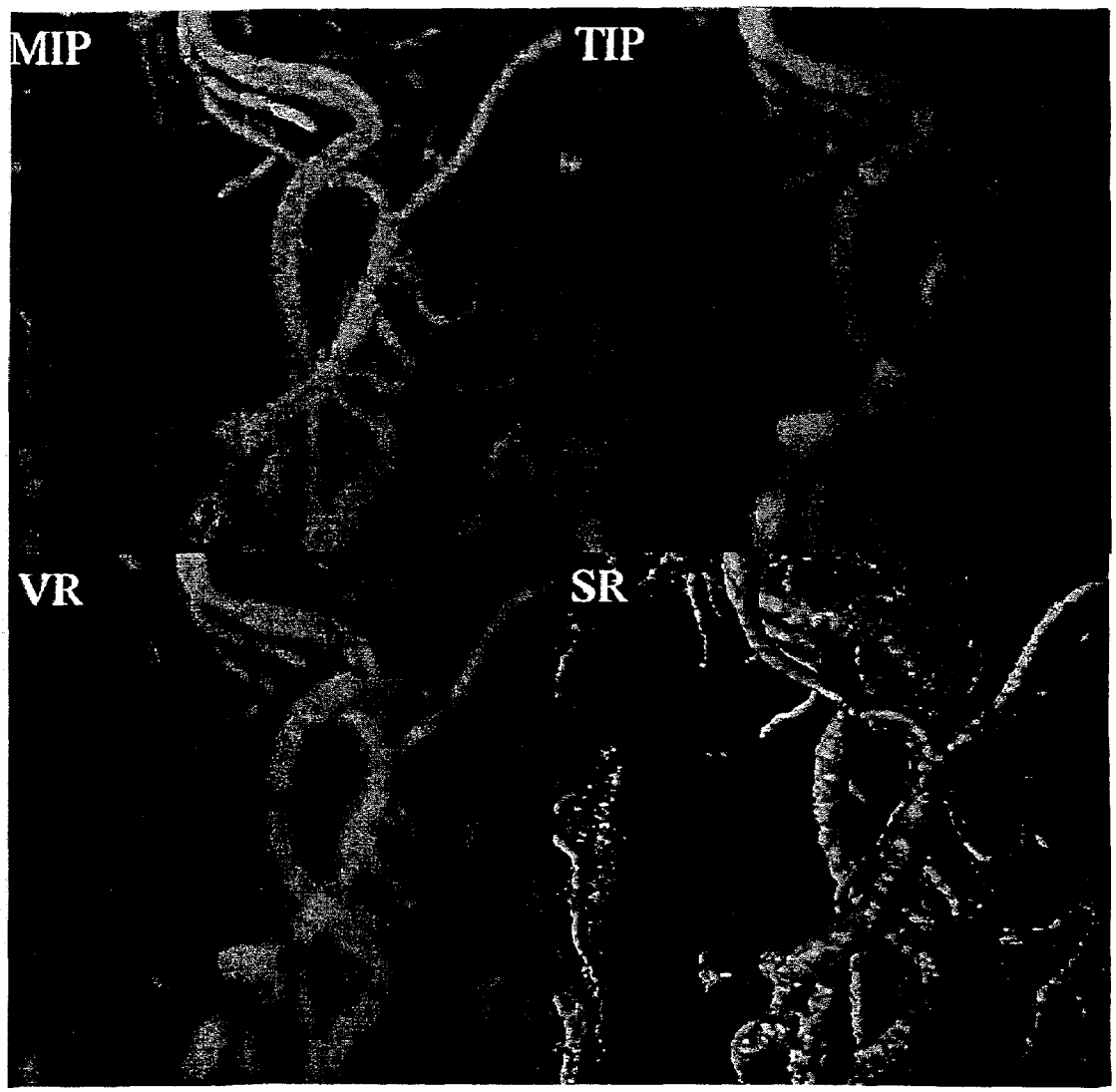
FIG. 2 illustrates a comparison between MIP, TIP, VR and SR methods.

FIG. 2 illustrated a comparison between MIP, TIP, VR, and SR images. The TIP image was derived by using $N_{NIP}=20$, i.e., 20 data points per imaginary ray were used to calculate the relevant pixel value in the NIP image. This can be viewed as setting a threshold for the value of data points to be used in pixel value calculations, as it in effect selects a data point value threshold that is exceeded by only 20 data points. Other ways of setting a threshold can be used instead, based on reasonable experimentation. In this case, the TIP image was calculated in accordance with the relationship TIP=MIP+$C_{TIP}$*NIP, where $C_{TIP}$ is a selectable coefficient or weighting factor of the type used in blending of two images that sometimes is referred to as alpha blending, and the symbol * signifies multiplication. For FIG. 2, $C_{TIP}=2$ was used to compute the TIP image from the MIP and NIP images. Normalization can be used as in conventional when combining a number of values into a single pixel value, and different weighting factors can be used for the data points used for the NIP image instead of the single weighting factor of 2 used in this example.

In FIG. 2, the TIP image shows increased spatial intensity where vessels overlap, but the conventional MIP image shows a cross-shaped artifact of ambiguous vessel take-off at the same location. The VR image shows similar depiction of vessel overlap as TIP but has increased structural background noise that can obscure smaller vessels. Perhaps more important from a practical usage point of view is that in this example the VR image took many trials, about 10 minutes, to adjust parameters using real time display and using the MIP image as a gold standard. The TIP image in this example took about 20 seconds to adjust because it started as a MIP image with linearly increased $C_{TIP}$ to the desired level. The surface rendered image shows the relative positions of the vessels for comparison.

Figure 3:
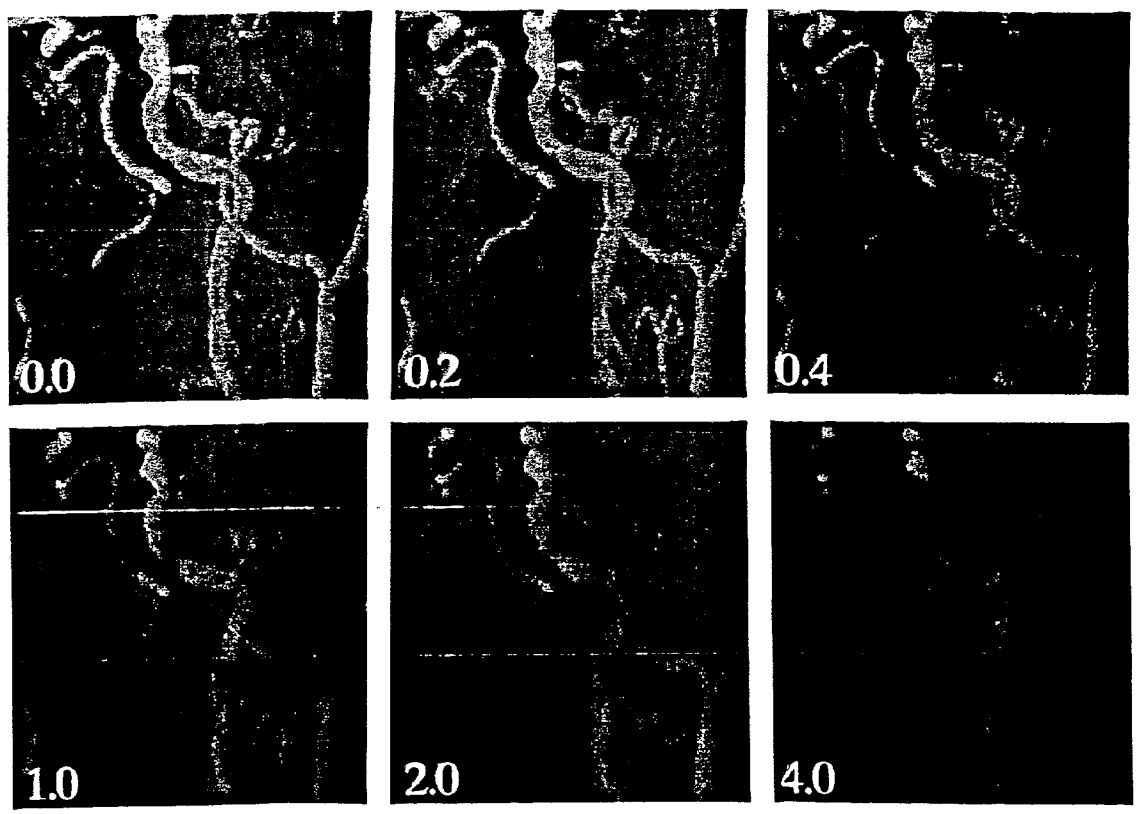
FIG. 3 illustrates linear combinations of MIP and NIP images, where the numerical values at each illustrated image is the ratio $C_{TIP}$=NIP/MIP). The degree of conspicuity of overlapping vessels increases with increasing ratios. The resulting images TIP are calculated, on pixel-by-pixel basis, as TIP=MIP+$C_{TIP}$*NIP.

FIG. 3 shows TIP images with different levels of $C_{TIP}$. As NIP weighting increases (i.e., the selected value of $C_{TIP}$ increases), there is an increased translucency of the vessels. This, however, is balanced against a decrease in the intensity of smaller vessels. The operator can adjust the TIP image by selecting the value of $C_{TIP}$ to a level that gives the desired balance at which the vessel overlap of interest is visualized well and yet smaller vessels of interest also are visible in the 2D TIP image. This is essentially a linear windowing operation of a single parameter that will vary for each MRA image data set that is processed, just as conventional window and level selections are made for viewing MR images. One technique is to initially set $C_{TIP}=0.0$ to obtain a MIP image, then adjusting window and level in the conventional way, then adjusting $C_{TIP}$ independently to a desired level, with vessel overlap clearly identifiable at $C_{TIP}=1.0$. In FIG. 3, the MIP image (at $C_{TIP}=0.0$) shows superposition of a branch of the external carotid over the larger internal carotid artery due to a greater intensity of the smaller carotid branch but there is ambiguity in other regions of vessel overlap.

Figure 4A:
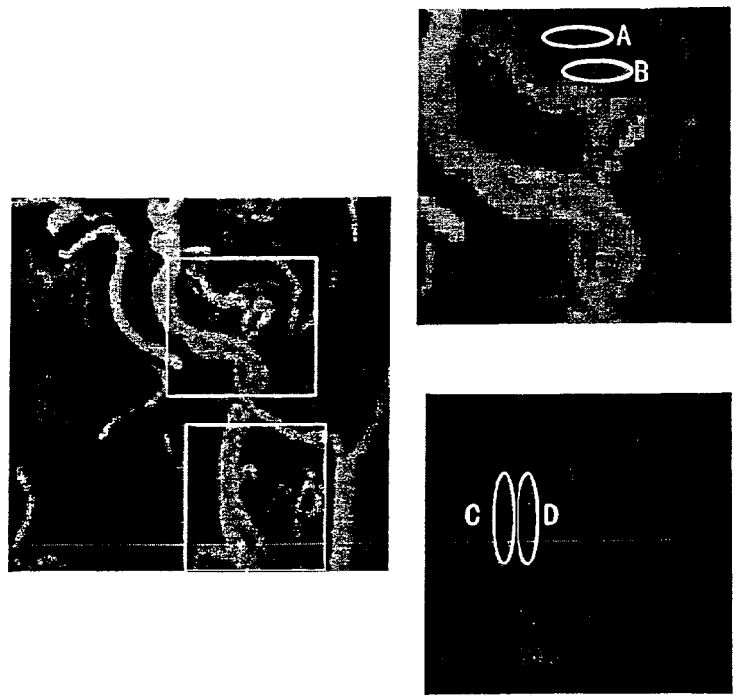
FIGS. 4a, 4b and 4c illustrate vessel overlap contrast assessment.
Figure 4B:
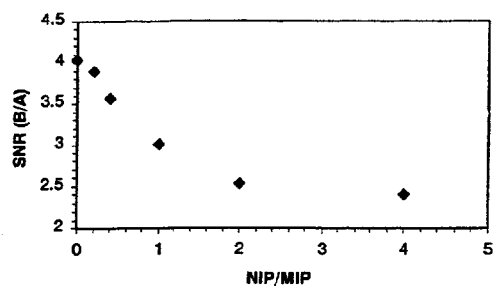
Figure 4C:
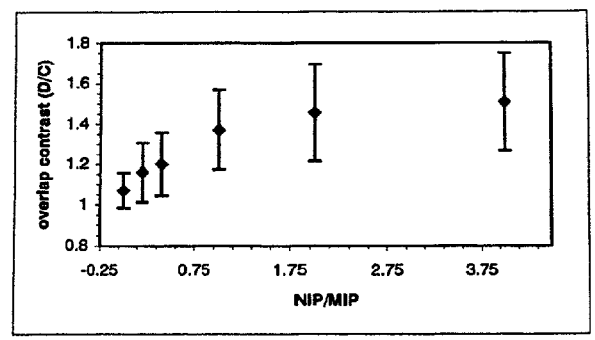

FIGS. 4a, 4b, and 4c relate to quantifying changes in CRN and vessel overlap conspicuity. A region of the carotid MRE (see FIG. 4a) was evaluated with regions of interest (ROI) measurements of signal intensity, where the regions are: A—background structured noise, B—small vessel, C—large vessel lumen, and D—overlap of vessels. FIG. 4b shows that the SNR of the small vessel changes with different $C_{TIP}$ (NIP/MIP) values. The plotted $C_{TIP}$ values correspond to images in FIG. 3, where $C_{TIP}=1.0$ clearly shows overlap of vessels. The FIG. 4b plot of small vessel SNR shows a 25% reduction of SNR at $C_{TIP}=1.0$. At this particular value, the SNR is sufficient to visualize the small vessel above structured background noise and there is a reliable visualization of vessel overlap. FIG. 4c shows that the contrast of vessel overlap increases with increased $C_{TIP}$.

Figure 5:
FIG. 5 illustrates a comparison between MIP, TIP and VR in an abdominal aortic aneurysm with stenosis of the common iliac arteries and atherosclerotic paques.

FIG. 5 shows comparative images of the aorta and renal arteries with presence of atherosclerotic plaques, common iliac artery stenosis and an aortic aneurysm. The MIP image show what appears to be a larger diameter origin to the iliac arteries whereas the TIP image shows smooth semilunar shaped intraluminal plaque extending from the aortic aneurysm into the left iliac artery. The VR image has a higher level of background structured noise that obscures the renal arteries. As the MIP image underestimates stenosis, the radiologist can look at the source images to confirm measurements. With the TIP image, however, there is an improved visualization of the internal plaques and stenosis such that the radiologist can make a better diagnosis directly from the projected TIP image.

Another application of TIP and LNIP is in the display of information from CT imaging, particularly spiral CT data of abdomen, pelvic and contrast enhanced vessel studies. 3D data sets of CT attenuation (Hounsfield) values of voxels in the patient volume can be processed in a manner analogous to the processing of the corrected set of 3D MRA data points discussed above to obtain a TIP and/or LNIP projections that enhance the visualization of desired features. Comparable 3D sets of data points, obtained by other imaging modalities, can also be similarly processed to obtain comparable TIP and LNIP 2D projections.

Thus, this patent specification discloses methods of obtaining 2D projective images from 3D data points sets that assign different weights to selected ones of the 3D data points that contribute to the values of related pixels in the 2D image in a way that enhances the visualization of selected features. Where the features of interest are blood vessels, the weighting scheme ensures visualization of small vessels while also providing clues in the 2D image of the relative depth of overlapping vessels.

LITERATURE CITED

1. Brown D G, Riederer S J, Contrast-to-noise ratios in maximum intensity projection images, Magn Reson Med 1992 January; 23(1):130–7
2. Parker D L, Chapman B E, Roberts J A, Alexander A L, Tsuruda J S, Enhanced image detail using continuity in the MIP Z-buffer: applications to magnetic resonance angiography., J Magn Reson Imaging 2000 April; 11(4): 378–88
3. Rice B L, Udupa J K, Cutter-free rendering for magnetic resonance angiography using fuzzy connectedness, Intern J. of Imaging Systems and Technology, 2000 v11, 1, 62–70
4. U.S. Pat. No. 5,297,551 Weighted ray projection imaging for MR angiography (Picker)
5. U.S. Pat. No. 5,368,033 Magnetic resonance angiography method and apparatus employing an integration projection
6. U.S. Pat. No. 4,984,160 Method for image reconstruction through selection of object regions for imaging by a comparison of noise statistical measure (GE CGR)
7. Guillaume R P, Thelissen, Maximum Average Projection (MAP): a fast and robust way to visualize 3-Dimensional MR data-sets. 1999 Book of Abstracts ISMRM
8. Ayanzen R H, Keller P J, Heiserman J E, A novel algorithm for the post processing of 2D TOF MRA, 1999 Book of Abstracts ISMRM, p1849.
9. Schmidt M, Hany T F, Gohde S C, Romanovski B, David C P, Debatin J F, Impact of 4 different post processing methods in the evaluation of contrast enhanced 3D MR-angiograms of the abdominal arteries, 1999 Book of Abstracts ISMRM, p1862.

What is claimed is:

1. A translucent intensity projection (TIP) method of MR imaging comprising:
   acquiring MR imaging data comprising values for volume elements (voxels) of a three-dimensional volume;
   using said data to form a two-dimensional projection image of values for picture elements (pixels) where respective pixel values are derived by combining values of said voxels that are along respective conceptual rays through respective voxels and pixels, and wherein said combining applies high weights to most intense voxel values along the rays and lower but still significant weights to other voxels along the same rays; and
   displaying an image related to said pixel values.

2. A method as in claim 1 in which said high and lower weights are representative of a weighting function having a selected shape.

3. A method as in claim 2 in which said weighting function is essentially monotonic.

4. A method as in claim 2 in which said weighting function has at least one flat portion.

5. A translucent intensity projection (TIP) method of MR imaging comprising:
   forming a maximum intensity projection (MIP) MR image and a matching net intensity projection (NIP) MR image
   combining said MIP and NIP images to form a TIP image having higher image contrast between small blood vessels and background than the NIP image but more visual clues to vessel depth than the MIP image; and
   displaying the TIP image.

6. A local net intensity projection (LNIP) method of MR imaging comprising:
   acquiring MR imaging data comprising values for volume elements (voxels) of a three-dimensional volume;
   using said data to form a two-dimensional projection image of values for picture elements (pixels) where respective pixel values are derived by combining values of said voxels that are along respective conceptual rays through respective voxels and pixels, and wherein said combining applies high weights to most intense voxel values along the rays and lower but still significant weights to other voxels along the same rays;
   said most intense voxel values along comprising values for more than one voxel when plural voxels values along a ray exceed a selected threshold; and
   displaying an image related to said pixel values.

* * * * *